United States Patent [19]

Zabsky et al.

[11] Patent Number: 5,185,532
[45] Date of Patent: Feb. 9, 1993

[54] DENTAL INSTRUMENT STERILIZER

[75] Inventors: John M. Zabsky, Santa Ana; Jerome Saitta, Los Angeles; Edward P. Bryan, Calabasas, all of Calif.

[73] Assignee: Oral Card Products, Los Angeles, Calif.

[21] Appl. No.: 703,797

[22] Filed: May 21, 1991

[51] Int. Cl.[5] .......................................... G01N 23/00
[52] U.S. Cl. .................................. 250/455.11; 422/24
[58] Field of Search ...................... 250/455.11; 422/24

[56] References Cited

U.S. PATENT DOCUMENTS

| | | | |
|---|---|---|---|
| 2,058,826 | 10/1936 | Reece | 250/455.1 |
| 3,820,252 | 6/1974 | Abernathy | 250/455.1 |
| 3,847,285 | 11/1974 | Leprince . | |
| 3,954,407 | 5/1976 | Andary et al. . | |
| 3,955,922 | 5/1976 | Moulthrop . | |
| 4,448,750 | 5/1984 | Fuesting | 250/455.1 |
| 4,625,119 | 11/1986 | Murdock, III | 250/455.1 |
| 4,740,706 | 4/1988 | Murdock, III | 250/455.1 |
| 4,874,952 | 10/1989 | Arnaud et al. | 250/455.1 |
| 4,888,487 | 12/1989 | Ritter | 250/455.1 |
| 4,906,851 | 3/1990 | Beasley et al. | 250/455.1 |
| 4,950,902 | 8/1990 | Ritter | 250/455.1 |
| 4,973,847 | 11/1990 | Lackey et al. | 250/455.1 |
| 5,034,235 | 7/1991 | Dunn et al. | 426/521 |

Primary Examiner—Bruce C. Anderson
Attorney, Agent, or Firm—Arthur Freilich; Robert D. Hornbaker; Leon D. Rosen

[57] ABSTRACT

A sterilizer is described that applies ultraviolet light to dental instruments such as slow and fast handpieces, picks, etc., which applies the light largely uniformly to the forward portions of the instruments which are used in patients' mouths. The apparatus includes a plurality of supports (21-24) that are each constructed to hold a dental instrument, with the supports each rotatably mounted on a frame about a different vertical axis (31-34). An ultraviolet light source (18) directs light primarily horizontally at the forward portions of the dental instruments to sterilize them.

8 Claims, 1 Drawing Sheet

DENTAL INSTRUMENT STERILIZER

BACKGROUND OF THE INVENTION

It is well recognized that the forward portions of dental instruments, which enter patients'mouths while the rearward portions are held in the dentist's hands, must be thoroughly sterilized after each use to prevent the spread of AIDS or other illnesses. Perhaps the most common method presently used is to insert the instruments in a bag that is placed in a dry heat sterilizer. The dry heat tends to dry out the bearings of handpieces, and is somewhat inconvenient because the handpieces must be cooled before use. It is well recognized that ultraviolet light can sterilize parts, with many ultraviolet light toothbrush sanitizers having been proposed. However, ultraviolet light can reliably sterilize only those areas of an item on which the light falls at high intensity, as where the light shines directly from an ultraviolet lamp onto the area. While the killing of most microorganisms is sufficient for use on toothbrushes, which will be reused by the same person, it is not sufficient for dental instruments which will be used on different unrelated patients. A sterilizer for dental instruments, which was compact, low cost, and easy to use, and which thoroughly sterilized the forward end portions of dental instruments, would be of considerable value.

SUMMARY OF THE INVENTION

In accordance with one embodiment of the present invention, apparatus is provided for sterilizing the forward portions of dental instruments. The apparatus includes a support which is mounted on a frame and which is constructed to hold a dental instrument, and an ultraviolet light source on the frame for illuminating the forward portion of the instrument. The support lies on one side of the ultraviolet light source, and is rotatable to expose the forward portion of the dental instrument to light from a wide variety of angles. The axis of rotation is preferably vertical, while the ultraviolet light moves largely horizontally from a lamp towards the forward portion of the instrument.

The apparatus can include a plurality of supports, each rotatable about its own axis, and each constructed to hold a dental instrument. Each support can include a permanently installed platform that is rotated by a motor, and a tubular holder that is detachably mounted on the support and which holds a dental instrument that extends substantially vertically within the tube.

The novel features of the invention are set forth with particularity in the appended claims. The invention will be best understood from the following description when read in conjunction with the accompanying drawings.

DESCRIPTION OF THE PREFERRED EMBODIMENT

Figure 1:
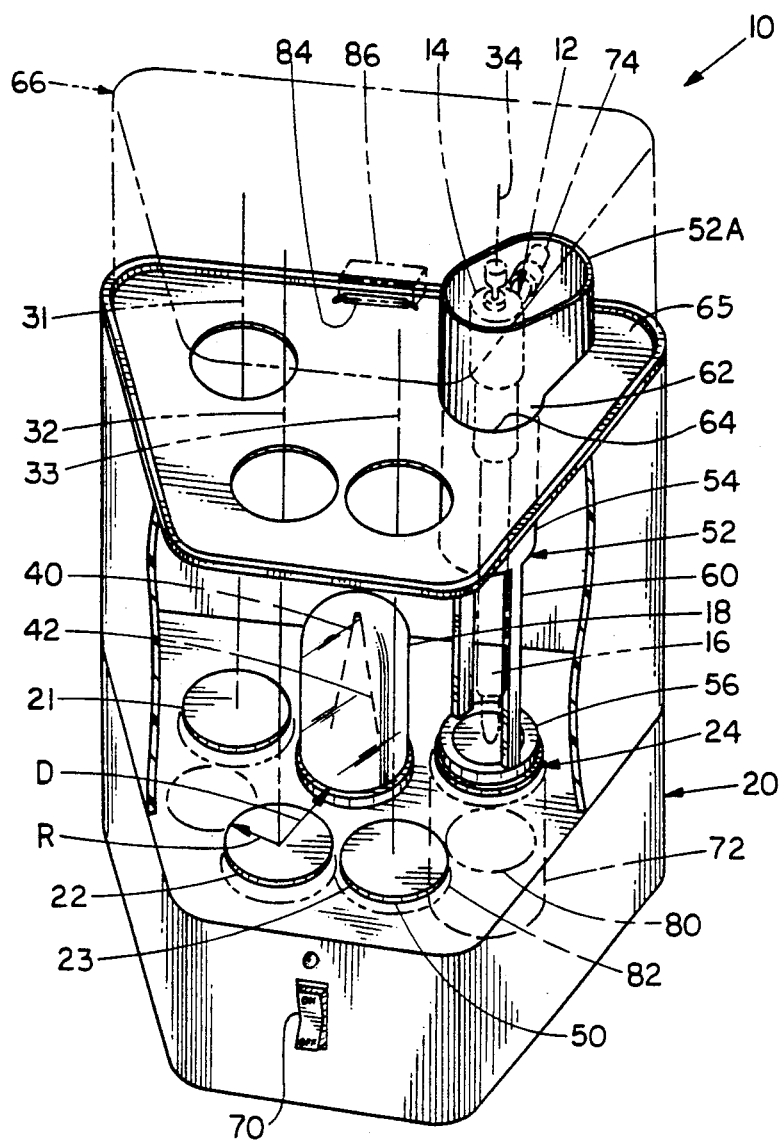
FIG. 1 is an isometric view of a dental instrument sterilizer constructed in accordance with the present invention, with a portion of the frame cut away, and with the cover shown in phantom lines.

FIG. 1 illustrates a dental instrument sterilizing apparatus 10 which can hold a dental instrument such as a slow hand piece 12 which has a rearward portion 14 that is held in a dentist's hand, and a forward portion 16 that sometimes lies in a patient's mouth. The apparatus is designed to sterilize the forward portion 16 of the dental instrument by the use of ultraviolet light from an ultraviolet lamp 18. The apparatus includes a frame 20 and four supports 21-24 rotatably mounted on the frame to expose all sides of the instrument forward portion 16 to ultraviolet light from the lamp.

Each support 21-24 rotates slowly (e.g. one rotation per minute) about its own vertical axis 31-34, which preferably passes either through or close to the dental instrument mounted on the support. As a result of such rotation, the forward portion of each dental instrument is exposed to direct ultraviolet light from a wide variety of angles. This avoids the presence of dental instrument regions that are not heavily exposed to ultraviolet light emitted directly from the lamp, and which may contain infectious agents. The lamp has filament portions 40, 42 that are at about the same height as the forward portions of the dental instruments, so light passes primarily horizontally from the lamp filaments toward the instrument forward portions, which is the most effective direction. With the elongated dental instrument extending substantially vertically, most of the outer surface of the instrument faces primarily horizontally, and primarily horizontal light rays are most effective in sterilization. Each support such as 22, has a radius R that is less than the radial distance D to the lamp, so that the support lies entirely on one side of the lamp.

Each support includes a platform 50 which is permanently rotatably mounted on the frame 20, and a holder 52 which is detachably mounted to the platform 50. The holder includes an elongated tube 54 with a base 56 that rests on the platform, so the platform can support the weight of the holder and dental instrument therein and rotate it. A lower portion 60 of the tube, of a height of a plurality of centimeters, is primarily open to enable the direct passage of light from the lamp 18 to the forward portion of a dental instrument that lies within the tube lower portion. An upper portion 62 of the tube extends through an opening 64 in a guide wall 65. The guide wall stabilizes the rotating holder to assure that it will not fall over. The top of the frame is covered by a removable cover 66.

Installation and removal of dental instruments in the apparatus is relatively simple. With the holder 52 outside of the frame, a dentist places a dental instrument in the holder, with the forward portion that will go into a patient's mouth, being lowermost. It is preferable to insert only one instrument in each holder. The dentist then removes the cover 66 and inserts the holder downwardly through an opening 64 in the guide wall 66, until the base 56 of the holder rests on a platform 50. A dentist then replaces the cover 66 and operates a switch 70 to cause energization of the ultraviolet lamp 18 and of a motor 72 slowly that turns all of the platforms. A timer causes the lamp and motor to be energized for a predetermined period such as 15 minutes, which will assure sterilization of the forward portion of the handpiece.

Figure 2:
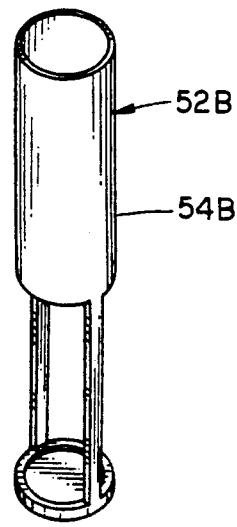
FIG. 2 is an isometric view of a dental instrument holder that can be used in the sterilizer of FIG. 1.

The apparatus 10 is designed to hold two types of holders, one type 52A being designed to hold a slow dental handpiece. A slow handpiece, wherein a bit holding shaft rotates relatively slowly (e.g. 1000 rpm), has primarily cylindrical portions, which also includes a tube 74 extending partially radially (perpendicular to the length of the handpiece which extends parallel to the axis 34) at the rearward portion of the handpiece. This results in a considerable width of the rearward portion of at least about two inches. As a result, applicant provides a holder 52A which can hold such a wide dental instrument, and spaces the platform of the support 24 a greater distance from an adjacent platform support 23 than the distance between two other platform supports 22, 23. For other dental instruments, applicant provides a different type of support shown at 52B in FIG. 2, which is substantially cylindrical, and can hold fast handpieces and a wide variety of probing instruments. The tube 54B of all of the holders are preferably formed of material that passes ultraviolet light, to sterilize even the rearward portion of the dental instrument, even if that portion is not sterilized as thoroughly as the forward portion. The tubes 54, 54B of FIGS. 1 and 2 are formed of material that passes ultraviolet light, but which still keeps the dental instrument extending substantially vertically so it does not fall over, that is, to limit tilt of the dental instrument while its weight is supported on the base 56. As shown in the drawings and discussed above, the height of the elongated tube 54 is a plurality of times the width of its base. The guide wall 66 is also preferably formed of material that passes ultraviolet light. More effective sterilization of the rearward portion of dental instruments can be achieved by the use of a tall ultraviolet lamp or more than one ultraviolet lamp.

Figure 3:
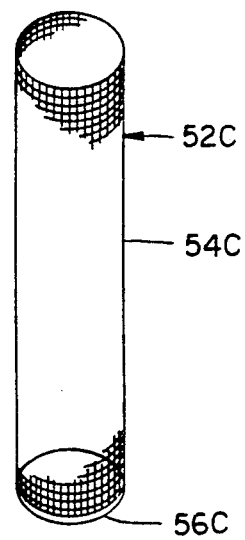
FIG. 3 is an isometric view of a dental instrument holder constructed in accordance with another embodiment of the invention, and that can be used in the sterilizer of FIG. 1.

FIG. 3 illustrates another holder 52C which includes a tube 54C formed of mesh, such as aluminum mesh, to pass most ultraviolet light along a considerable height of a vertically-oriented dental instrument. The holder 52 has a base 56C which can rest on any of the platforms of the apparatus of FIG. 1.

The motor 72 can be coupled to the four platforms in a variety of ways, such as through a belt or gears. FIG. 1 shows a gear train including gears such as 80, 82 that couple the bases of the supports to rotate each of them about its corresponding axis. The apparatus is constructed to prevent operation until the cover 66 is placed over the frame, to prevent persons from directly viewing the ultraviolet lamp through the opening 64. To this end, the apparatus includes a magnetic reed switch 84 which is closed only when a magnet 86 mounted on the cover lies adjacent to the switch. Applicant prefers to construct the cover 66 of a material which is transparent to some visual wave lengths of light, while blocking out ultraviolet light, to enable the dentist to see how his equipment is working. Also, windows of ultraviolet-light blocking material can be provided to enable viewing the lower portions of the supports.

Figure 4:
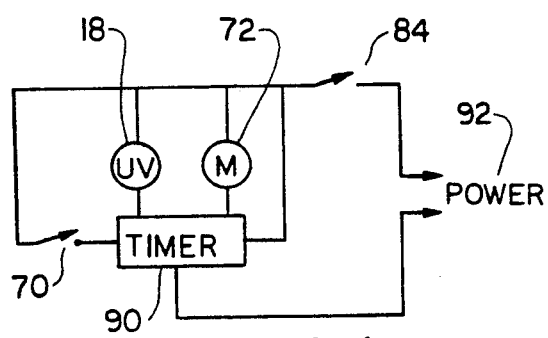
FIG. 4 is a simplified diagram of the electric circuit of the sterilizer of FIG. 1.

FIG. 4 is a simplified schematic diagram of the circuitry of the apparatus. The circuit includes a timer 90 which is started when the switch 70 is closed (providing the reed switch 84 is also closed). The timer 90 delivers current from a power source 92 through the lamp 18 and motor 72 for a predetermined period of time such as 15 minutes. The timer is preferably controllable to set any period within a wide range.

Thus, the invention provides relatively simple, compact, and economical apparatus for sterilizing at least the forward portions of dental instruments. The apparatus includes an ultraviolet light source and supports for holding dental instruments so they are illuminated by the light source. Each support is rotatable about its own vertical axis to expose all areas of the dental instrument forward portion to direct ultraviolet light from a wide variety of angles. The apparatus can include platforms that are each rotatable about an individual axis, and a holder that is detachably mounted to the platform. The holder can be in the form of a tube with most of the area of its lower portion being open to the passage of ultraviolet light.

Although particular embodiments of the invention have been described and illustrated herein, it is recognized that modifications and variations may readily occur to those skilled in the art, and consequently, it is intended that the claims be interpreted to cover such modifications and equivalents.

We claim:

1. Apparatus for sterilizing the forward portion of at least one dental instrument which has a forward portion that enters a patient's mouth and a rearward portion that is held by a dentist in the usual use of the instrument, comprising:

a frame;

a support mounted on said frame, said support being constructed to hold a dental instrument;

an ultraviolet light source mounted on said frame and largely horizontally spaced from said support to illuminate the forward portion of a dental instrument thereon;

said support being rotatable about a vertical axis which is horizontally spaced from said light source, and with the radius of said support being less than the distance between said axis and said light source, so as the support rotates all sides of said dental instrument forward portion are exposed to said light source;

a motor coupled to said support to rotate it about said axis;

said support having a base of predetermined width which supports the weight of a dental instrument without preventing it from tilting, and said support forming a tube which extends above said base by a distance which is a plurality of times said width to limit tilting of the dental instrument.

2. The apparatus described in claim 1 including:

at least one additional support constructed to hold an additional dental instrument, said additional support being rotatably mounted on said frame about its own second vertical axis and being coupled to said motor, and said additional support being in the form of a tube having a greater height than width.

3. The apparatus described in claim 1 wherein said support includes a platform and a holder detachably mountable to said platform, said holder comprising an elongated tube with a base that rests on said platform and with a lower portion extending a plurality of centimeters above said base which is primarily open to enable the direct passage of light from said source to a dental instrument forward portion that lies within said tube lower portion.

4. The apparatus described in claim 1 wherein:

said support includes a platform and an elongated tubular holder for holding a dental instrument, said holder being detachably mountable to said platform to extend upwardly from said platform;

said frame includes a guide spaced above said platform and having an opening that closely surrounds said tubular holder to stabilize its orientation on said platform.

5. Apparatus for sterilizing the forward portions of dental instruments that each have a forward portion intended to enter a patient's mouth and a rearward portion intended to be held by a dentist, comprising:
 a frame;
 a plurality of supports mounted on said frame, each support being constructed to hold a dental instrument with the forward portion thereof lying at approximately a predetermined location;
 an ultraviolet light source positioned to shine light at said locations of all of said supports;
 each support being rotatably mounted on said frame about a different axis, with said axes being spaced from one another;
 a motor coupled to said supports to rotate each support about a corresponding one of said axes;
 each of said supports includes a platform and a vertically elongated tubular holder which is detachably mountable to said platform to extend upwardly from said platform.

6. The apparatus described in claim 5 wherein each of said dental instruments is elongated, and each said tubular holder is constructed to hold a dental instrument extending primarily parallel to the axis of rotation of that support, with each tubular holder having a base that supports the weight of the dental instrument and an upstanding portion that limits tilt of the dental instrument.

7. The apparatus described in claim 5 wherein a first of said supports is constructed to hold a slow handpiece dental instrument which has primarily cylindrical portions but which includes a tube extending partially radially at said rearward portion to leave a rearward portion of a width of at least about two inches, and the axis of said first support is spaced further from any other one of said axes than the spacing of the axes of second and third of said supports.

8. A method for sterilizing the forward portions of dental instruments that each have a forward portion intended to enter a patient's mouth and a rearward portion intended to be held by a dentist, comprising:
 mounting each of a plurality of dental instruments on one of a plurality of separate supports, with said supports comprising a plurality of platforms largely horizontally spaced from each other;
 directing ultraviolet light at each of said supports;
 rotating each of said supports about a separate vertical axis extending substantially through that support while directing said light at that support;
 said step of mounting including placing each instrument in a vertically elongated tube which has a base that supports the weight of the instrument and side walls that limit tilt of the instrument, and then placing the tube on one of said platforms.

* * * * *